(12) United States Patent
Mueller-Fiedler et al.

(10) Patent No.: US 6,668,104 B1
(45) Date of Patent: Dec. 23, 2003

(54) OPTICAL SENSOR

(75) Inventors: Roland Mueller-Fiedler, Leonberg (DE); Helmut Sautter, Ditzingen (DE); Winfried Bernhard, Gerlingen (DE); Andre Mueller, Gerlingen (DE); Lutz Mueller, Gerlingen (DE); Rainer Schink, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/554,347

(22) PCT Filed: Sep. 15, 1999

(86) PCT No.: PCT/DE99/02916

§ 371 (c)(1),
(2), (4) Date: Jul. 24, 2000

(87) PCT Pub. No.: WO00/15478

PCT Pub. Date: Mar. 23, 2000

(30) Foreign Application Priority Data

Sep. 15, 1998 (DE) .......................................... 198 42 063

(51) Int. Cl.[7] ................................................. G02B 6/00
(52) U.S. Cl. ............................. 385/12; 385/15; 385/31
(58) Field of Search ............................... 385/12, 31, 15

(56) References Cited

U.S. PATENT DOCUMENTS

| | | |
|---|---|---|
| 3,947,131 A | 3/1976 | Karl |
| 4,661,320 A | 4/1987 | Ito et al. |
| 5,565,978 A | 10/1996 | Okubo et al. |
| 5,747,348 A | 5/1998 | Jaduszliwer et al. |
| 6,307,198 B1 * | 10/2001 | Asakura et al. ........ 250/227.25 |

FOREIGN PATENT DOCUMENTS

| | | |
|---|---|---|
| DE | 41 02 146 C | 9/1991 |
| DE | 42 42 435 A | 1/1994 |
| EP | 0 562 275 A | 9/1993 |
| EP | 0 869 043 A | 10/1998 |
| FR | 2 672 127 A | 7/1992 |
| WO | 91 10122 A | 7/1991 |

* cited by examiner

Primary Examiner—Rodney Bovernick
Assistant Examiner—Sung Pak
(74) Attorney, Agent, or Firm—Michael J. Striker

(57) ABSTRACT

An optical sensor for detecting wetting of a surface (11), In particular of a vehicle window, has at least one transmitter (13) and at least one receiver (15) for electromagnetic waves, the surface being located in a sensor region (16) between the at least one transmitter (13) and the at least one receiver (15). The development of wetting on the sensor region (16) of the surface (11) causes a signal change. The optical sensor has a light-carrying element (18), in which the electromagnetic waves are guided bidirectionally into the sensor region (16) and out of the sensor region (16), and a retroreflector (10) is disposed in the sensor region (16) in such a way that it returns the electromagnetic waves, reflected before the surface (11), back to the surface (11) and from there to the light-carrying element (18).

15 Claims, 7 Drawing Sheets

Fig. 8a
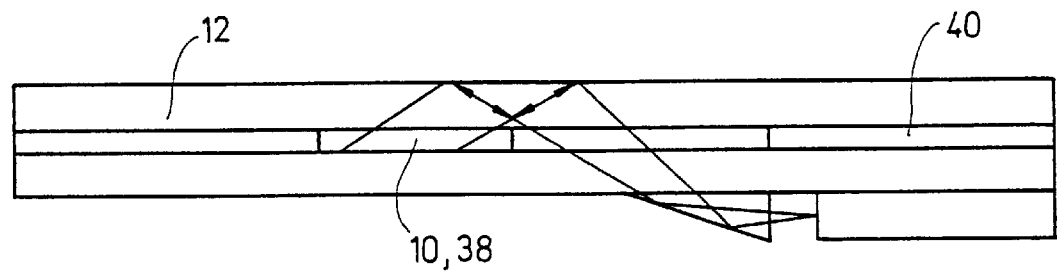
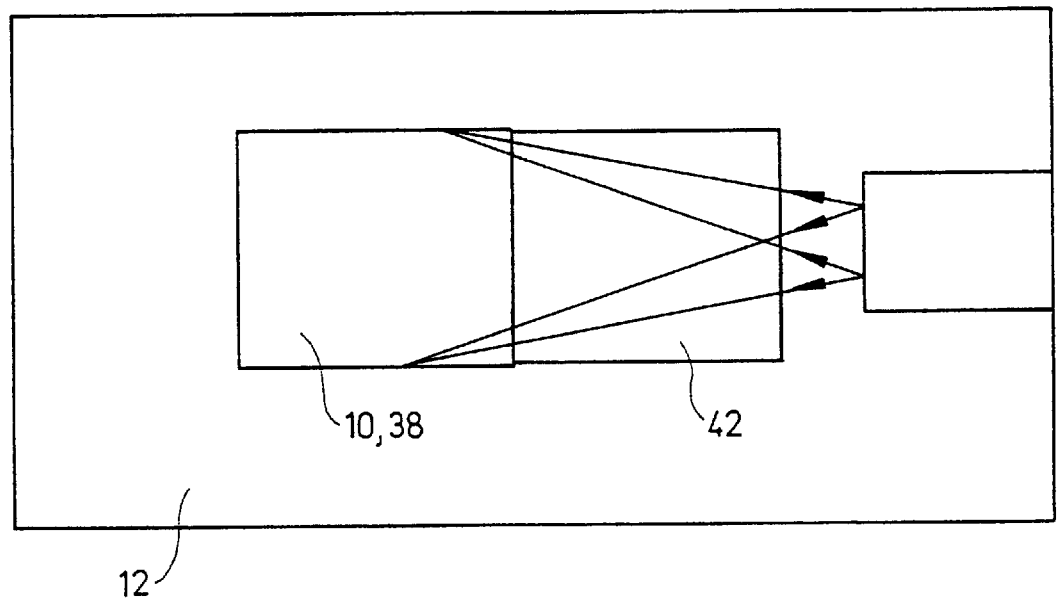
Fig. 8b

OPTICAL SENSOR

BACKGROUND OF THE INVENTION

The invention relates to an optical sensor for detecting wetting of a surface.

PRIOR ART

Optical sensors of this generic type are known. They serve for instance to control a motor vehicle light system and/or windshield wiper system. Measurement value detection is done essentially by an optoeletronic principle. Light from the visible range or the infrared range is coupled into the windshield from the inside of the windshield. The unmoistened outer surface reflects the light, which reaches a receiver. To increase the efficiency, the light is shone in in such a way that total reflection takes place on the outside. The total reflection is disturbed by the wetting of the outer surface with water. It is a common feature of all the known versions that the input and output of the electromagnetic waves take place at spatially markedly separate points, and that the sensor element and the evaluation electronics are accommodated in a common housing.

Error-free signal detection can then be accomplished only if the optical sensor is mounted in a region of the windshield that is cleaned by the windshield wiper system. Therefore in some vehicle types, the sensor has to be mounted at a distance of up to 15 cm from the upper edge of the windshield. A disadvantage of this is that the sensor housing in these cases is within the field of view of the driver and is perceived as annoying because of the lack of transparency. Miniaturization is not possible, since for timely detection of wetting, for instance when it is beginning to rain, a sensor region approximately 4–5 cm$^2$ in area is necessary.

SUMMARY OF THE INVENTION

The optical sensor of the invention having the characteristics of the main claim has the advantage in particular that the sensor region need not be disposed immediately where the evaluation electronics are. Because the light is carried between the at least one transmitter and the at least one receiver bidirectionally to the sensor region via a light-carrying element, and a retroreflector is disposed in the sensor region, the sensor region can be disposed at a distance from the transmitter or receiver. The reflection of the sensor signals occurs at the retroreflector, which is preferably shaped from a transparent material. The sensor components that for technical reasons cannot be made from a transparent material, in particular the transmitter and the receiver, can now, in a preferred use as a rain sensor, be disposed outside the field of view of the driver. Thus the visual appearance of the sensor, particularly if it is used as a rain sensor in motor vehicles, can be designed to be less noticeable. Furthermore, a common input and output point of the light is obtained.

Advantageous embodiments for the light-carrying element are monomode or multimode optical waveguides of glass or plastic, either singly or in bundled form. Also plates or suitably shaped bodies of glass or plastic, shaped so that they can carry light. To optimize the light carrying, it is advantageous to apply a coating to the light-carrying element that has a coefficient of refraction that is less by at least a few percent than the light-carrying element. As a result, the total reflection required for carrying light does not take place at the surface of the light-carrying element but rather at the boundary face between the coating and the core material of the light-carrying element. The delivery and return of the light can also be done via one common optical waveguide or separate optical waveguides that are disposed side by side or one above the other.

For inputting the beam of light from the light-carrying element into the windshield and vice versa, a coupling element is provided, which can preferably also be embodied in one piece with the light-carrying element. The beam of light is deflected in such a way that it meets the boundary face of the surface with at least the limit angle of the total reflection. Advantageous embodiments can be elbows, prisms, or a roughened underside of the light-carrying element.

The reflection of the beam of light is advantageously effected via prismatic reflectors. They can be preferably disposed as microstructures with dimensions between 2 µm and 100 µm in circular segments or in strips. Instead of a prismatic reflector, a reflective dye or glass beads embedded in plastic can also be used. If transparency is not necessary, then the prisms can preferably be replaced by mirrored surfaces, and in particular by concave mirror segments, which focus the beam of light onto the output point.

The reflection can also be achieved a hologram that is applied to the window or is for instance glued in the form of a film into the windshield. This provides mechanical protection of the hologram, and the windshield need not have something glued to its inside surface. Furthermore, the hologram film on the surface of the windshield cannot cause any light reflections, and thus it is not so visible to the driver and is thus less annoying.

A further option is for the adhesive film disposed in the windshield to be embodied itself as a hologram film in a suitable region. It is also especially advantageous that the present sensor principle can be employed in slightly modified form to prove the presence of various kinds of measurement substances, in the form of liquid, aerosol, in solution, or in gaseous form. Then a substance is applied in the sensor region that in the presence of the measurement substance reacts by changing its coefficient of refraction or color. The resultant refraction, absorption or reflection of the beam of light in the sensor region causes a signal change, which can be recorded in the receiver. In this embodiment, retroreflectors and the substrate of the sensitive substance can preferably be embodied as a structural unit.

It is also advantageous that because of the spatial separation of the electronics and the retroreflector, a harmful influence of the measurement substance on the components of the electronics can be averted, since the contact with the measurement substance takes place only via the sensor region. The material comprising the substrate can preferably be glass or a transparent plastic. What is essential is that this body have a surface at which total reflection occurs.

The construction according to the invention makes it possible for there to be markedly fewer components in the region of the primary measurement value detection. As a result, a greater range of variation of the sensor shape and size is also attained.

Further preferred features will become apparent from the other characteristics recited in the dependent claims.

BRIEF DESCRIPTION OF THE DRAWINGS

The invention will be described in further detail below in terms of exemplary embodiments in conjunction with the drawings. Shown are:

FIGS. 8a and 8b, a sectional and plan view on a windshield in the sensor region.

DETAILED DESCRIPTION OF THE PREFERRED EMBODIMENTS

Figure 1:
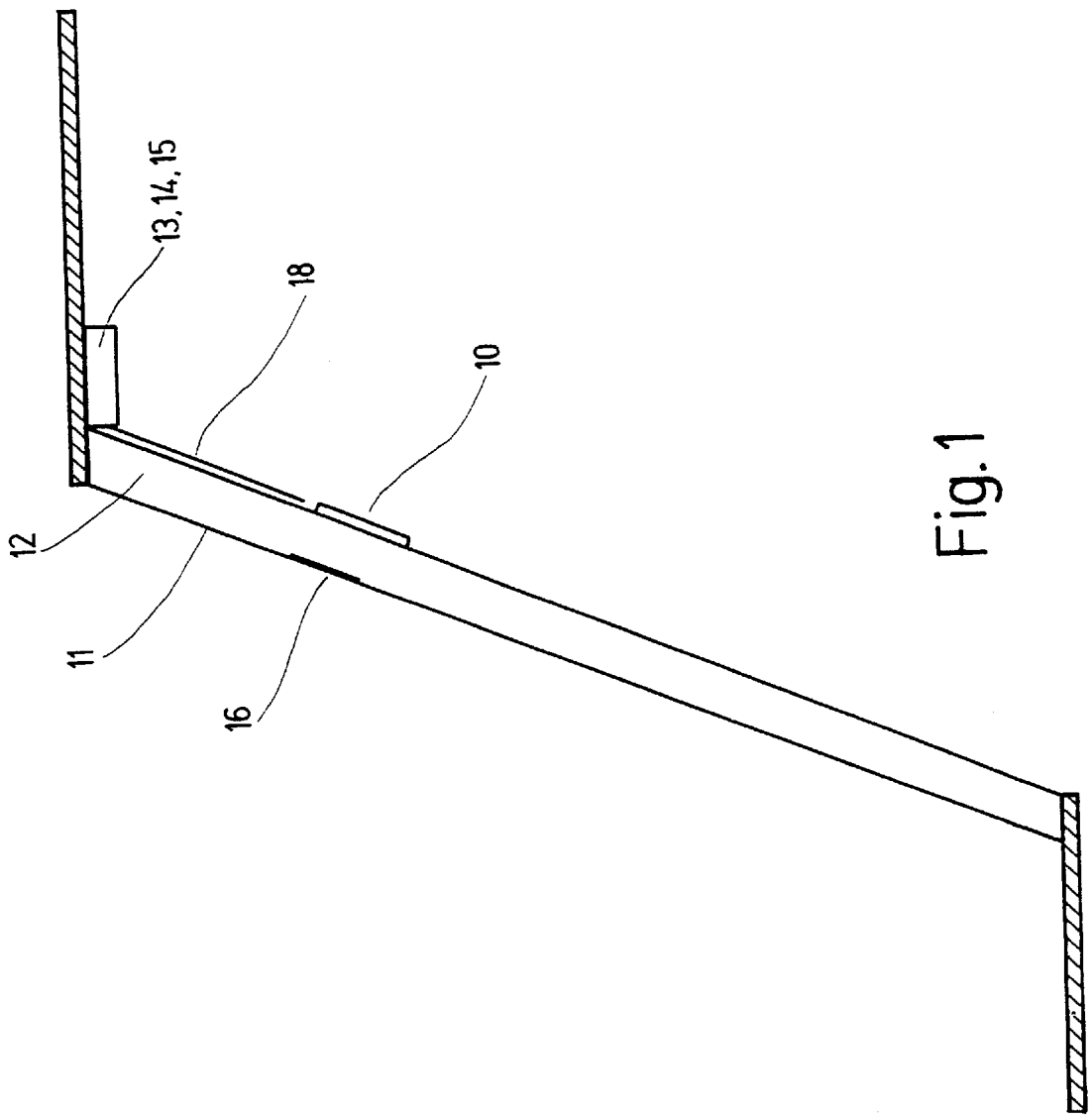
FIG. 1, a schematic overall view of the disposition of an optical sensor on the windshield of a motor vehicle.

FIG. 1, in a schematic overall view, shows the disposition of an optical sensor on a windshield 12 of a motor vehicle. A retroreflector 10 and a light-carrying element 18 are mounted on the inside of the windshield 12, for instance by adhesive bonding. The surface 11 of the outside of the windshield 12, where light is reflected in a manner to be described hereinafter, defines a sensor region 16. A housing 14 for an electronic system, which includes at least one transmitter 13 and at least one receiver 15, is located spatially remote from the retroreflector 10 and thus is moved away from the field of view of a driver. The electronic system is for instance integrated into the base of an inside rear view mirror.

Figure 2:
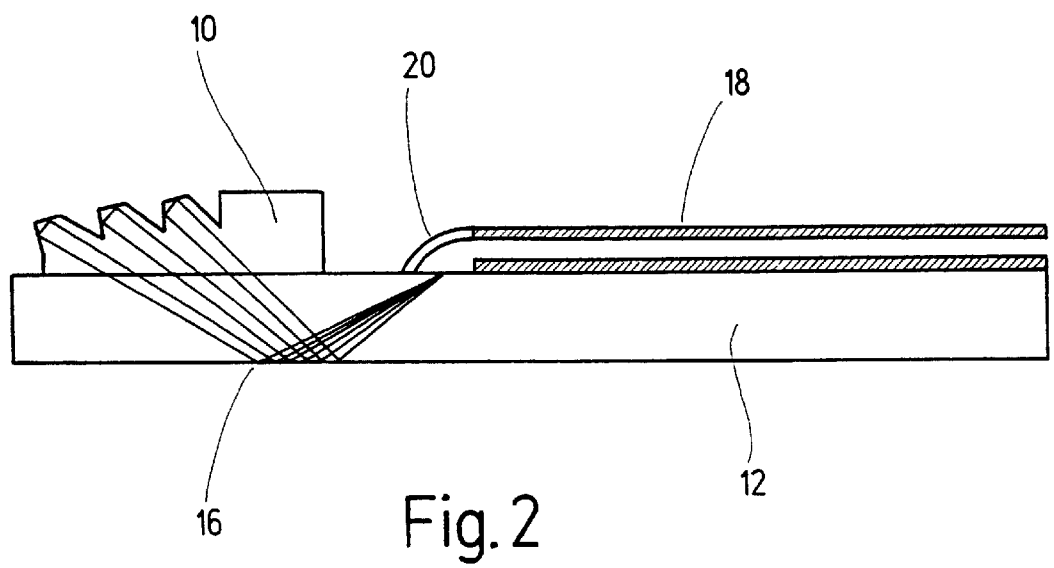
FIG. 2, an enlarged detail of FIG. 1.

FIG. 2 shows a schematic fragmentary sectional view of the optical sensor as a rain sensor on the windshield 12 of a motor vehicle. The elements of the sensor, that is, the light-carrying element 18 and the retroreflector 10, are mounted on the inside of the windshield 12. The light-carrying element 18 guides the light, which is generated by the at least one transmitter, via a coupling element 20, where the light is deflected in such a way that at least the limit angle of total reflection is attained at the outer glass boundary face. The light is then returned via the prismatic retroreflector 10 and via the outer surface 11 of the window 12 and again via the coupling element 20 enters the light-carrying element 18 and is carried by it to the at least one receiver 15. If the sensor region 16 is wetted with a liquid, the coefficient of refraction increases in this region, which leads to a reduction in the intensity of the reflected beam of light at the receiver 15, since the total reflection fails to occur in the sensor region. The present embodiment makes it possible to perform the signal processing spatially separately from the sensor region 16.

Figure 3:
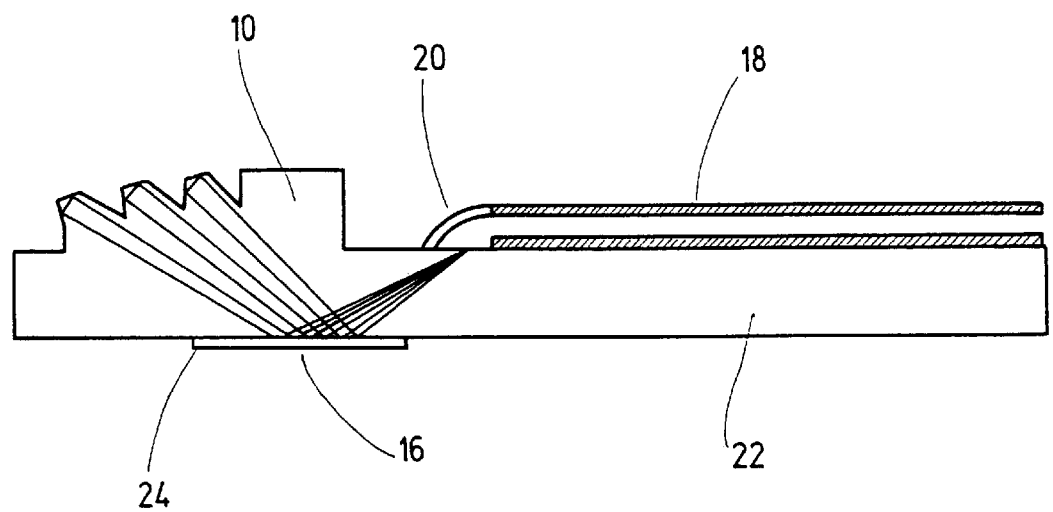
FIG. 3, a further use of the optical sensor.

FIG. 3, in a schematic fragmentary sectional view, shows a slightly modified embodiment that can be used to prove the presence of various kinds of substances. The light wave guidance is effected here in the same way as in the version described in FIG. 2. The sensor region 16 is coated here with a sensor-active substance 24. The presence of a measurement substance, which is preferably in the form of liquid, aerosol, in solution, or in gaseous form, can lead to a change in the coefficient of refraction or the color in the sensor region 16. This effect can be attained for instance via a chemical reaction or completing. The result is again a change in intensity of the reflected light beam at the receiver 15. The retroreflector 10 and a substrate 22 of the sensor material can be combined into a unit.

Figure 4A:
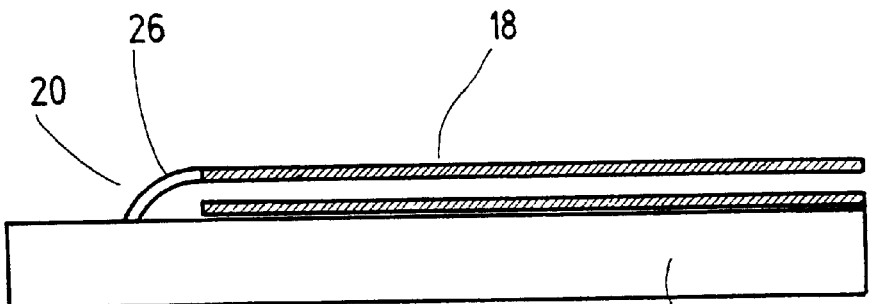
FIGS. 4a–4c, various versions of a coupling element.
Figure 4B:
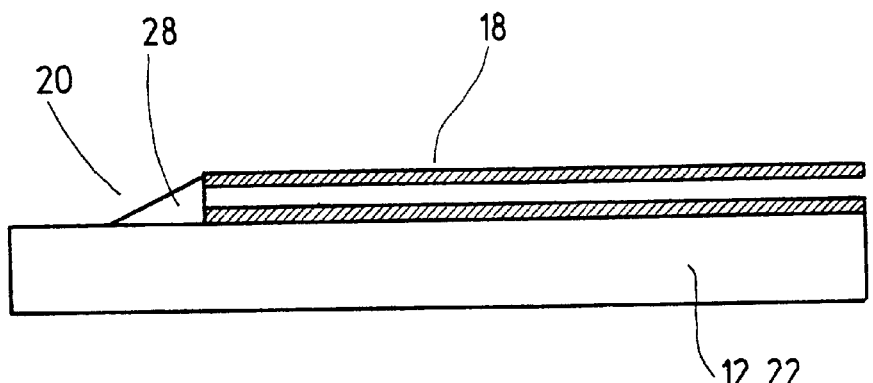
Figure 4C:
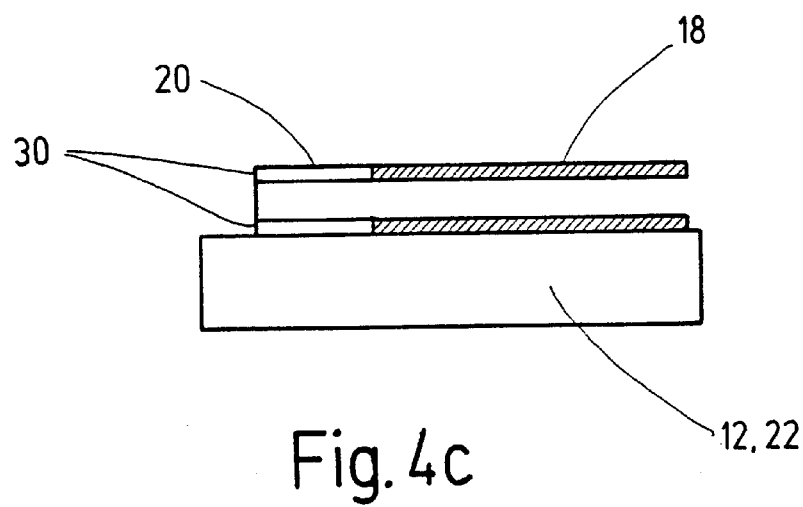

FIGS. 4a–4c, in a schematic sectional view, show three different embodiments of the coupling element 20. The light brought parallel to the surface of the substrate 22 or the windshield 12 via the light-carrying element 18 is reflected here in such a way that at least the limit angle of total reflection is attained at the outer boundary face. Alternative embodiments are an elbow 26 (FIG. 4a), a prism 28 (FIG. 4b), or a structuring 30 of the optical waveguide 18 (FIG. 4c) by roughening or by impressing grating-like structures into it. This structuring can be applied to the underside or topside of the end of the optical waveguide, specifically in such a way that it faces toward the substrate 22 or the windshield 12; in this case, losses in light intensity necessarily occur.

Figure 5A:
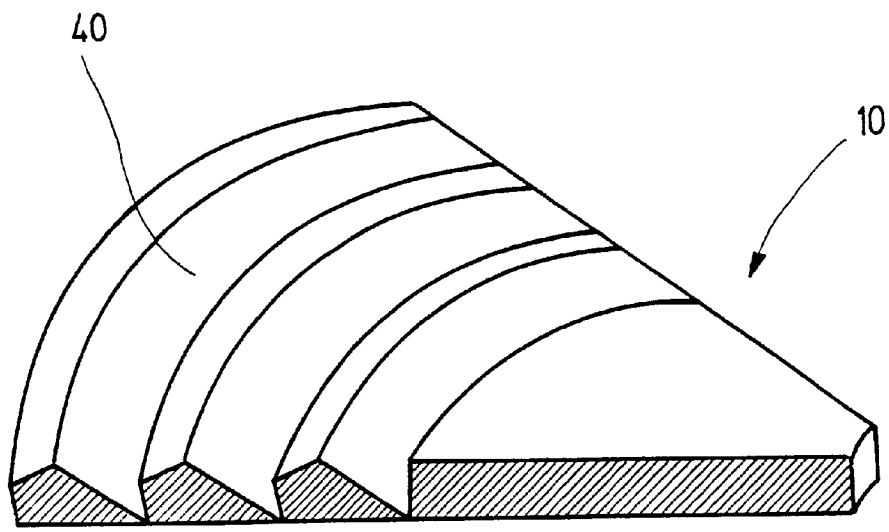
FIGS. 5a and 5b, various versions of a prism retroreflector.
Figure 5B:
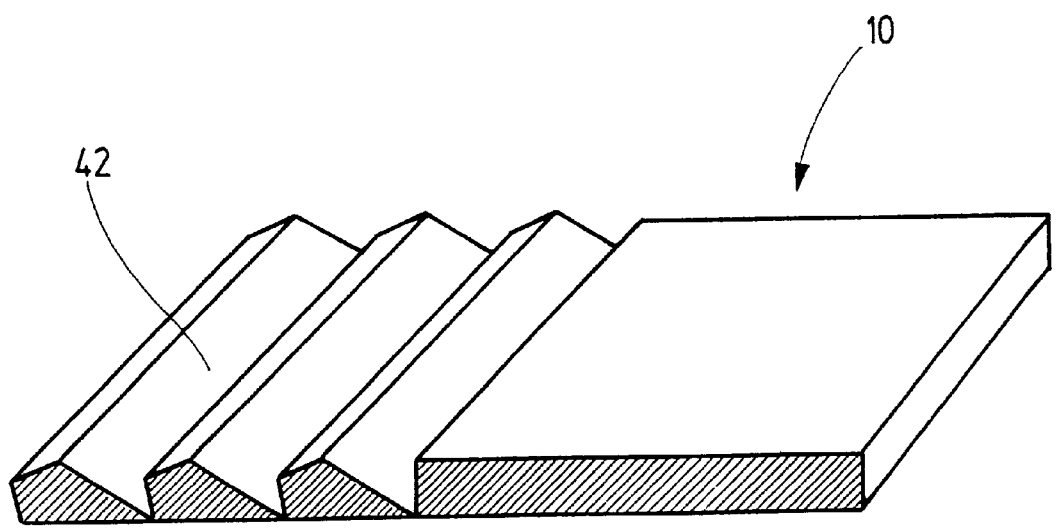

FIGS. 5a and 5b show two alternative versions, in perspective views of the retroreflector 10. In FIG. 5a, the prisms 40 required for the reflection are disposed in segments of a circle. FIG. 5b, conversely, shows a striplike arrangement of the prisms 42. The size of these microstructures (prisms) can preferably range between 2 $\mu$m and 100 $\mu$m.

Figure 6A:
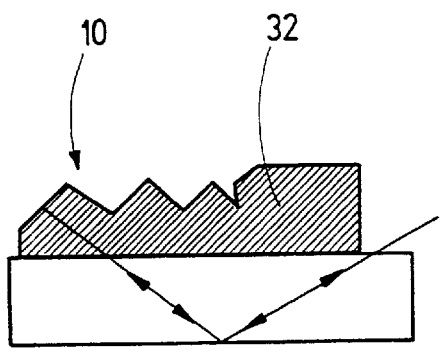
FIGS. 6a–6d, various versions of the retroreflector.
Figure 6B:
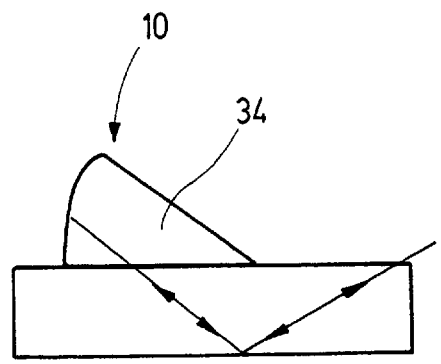
Figure 6C:
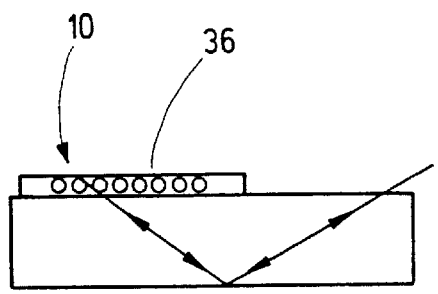
Figure 6D:
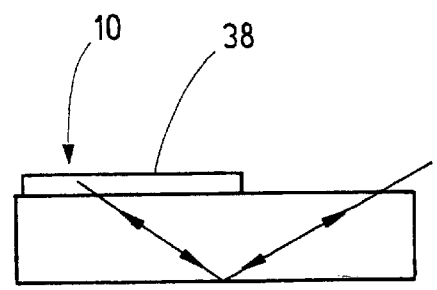

In FIGS. 6a–6d, further alternative embodiments of the retroreflector are shown in schematic sectional views. FIGS. 6a and 6b show mirror segments 32 and concave mirror segments 34, which focus the light at the output point. The mirror surfaces must be at least partly metallized, and this embodiment is therefore limited to applications in which transparency is not required. For reflecting the beam of light, it is also possible to use glass beads 36 embedded in a plastic, or a reflective dye, as schematically shown in FIG. 6c. In FIG. 6d, the reflection takes place via a schematically illustrated hologram 38, which is applied in the form of a plate, film or flat pane of glass.

Figure 7A:
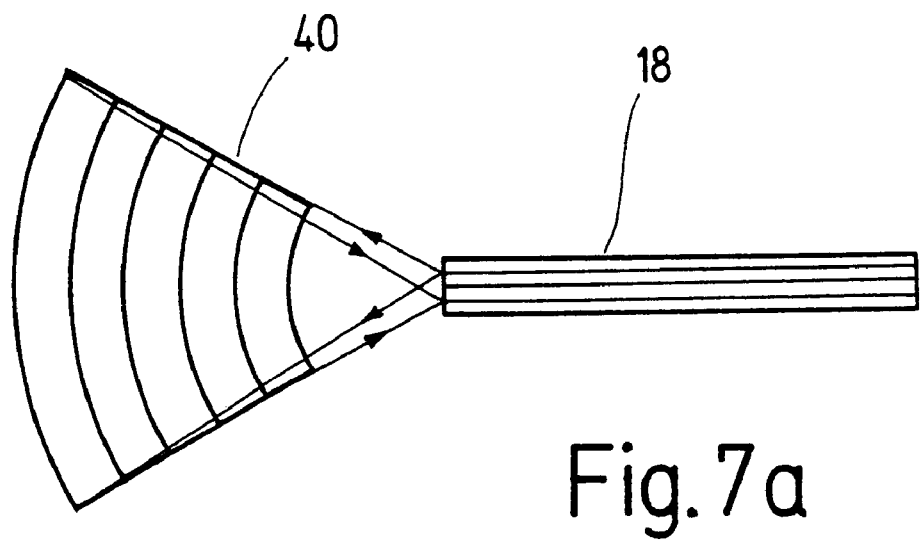
FIGS. 7a and 7b, various versions of the optical waveguide.
Figure 7B:
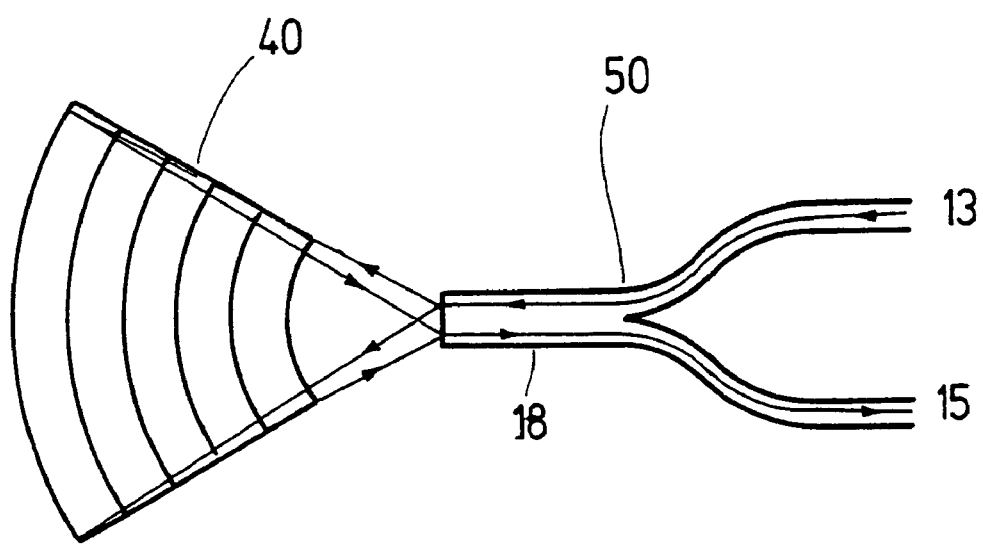

In FIGS. 7a and 7b, two alternative versions of the optical waveguide 18 are shown. The delivery and return of the beam of light, which is reflected for instance at the schematically illustrated circular-segmental retroreflector, can be done in two ways here. Either there are separate optical waveguides 18, which are disposed side by side or one above the other (FIG. 7a), or the beam of light is guided to the coupling 10 element 20 via a common optical waveguide, with a beam splitter 50 disposed upstream of the transmitter 13 or the receiver 15.

In FIG. 8a, a windshield 12 is shown in section and in FIG. 8b a windshield 12 is shown in plan view, both schematically.

If an infrared light (IR) is used as the light for detection purposes, then the IR-impermeable adhesive film 40 disposed in the windshield 12 must be cut away in the sensor region 16, to assure the passage of the detection light through it.

The hologram 38 is located in the windshield 12, and in particular in a portion of this cutaway area 42; the remaining area remains empty or is filled with an IR-permeable adhesive film. The IR light enters the windshield 12, is admitted in the IR-permeable region of the cutaway area 42, is totally reflected at the surface of the windshield 12, is reflected in the entry direction at the hologram 38, and after another total reflection at the surface of the windshield 12 is guided through the IR-permeable region of the cutaway area 42 into the receiver 15.

What is claimed is:

1. An optical sensor for detecting wetting of a surface (11), in particular of a vehicle window, comprising at least one transmitter (13) and at least one receiver (15) for electromagnetic waves, the surface being located in a sensor region (16) between the at least one transmitter (13) and the at least one receiver (15), wherein the development of wetting on the sensor region (16) of the surface (11) causes a signal change, wherein the optical sensor has a light-carrying element (18), in which the electromagnetic waves are guided bidirectionally into the sensor region (16) and out of the sensor region (16) in such a way that it returns the electromagnetic waves, reflected from the surface (11), back to the surface (11) and from there to the light-carrying element (18), wherein the light-carrying element (18) is a monomode or multimode optical waveguide, wherein a retroreflector (10) is provided and formed of a hologram (38) in the form of a plate or film, and wherein the disposition of the reflective segments of the retroreflector (10) is circular or striplike.

2. The optical sensor of claim 1, wherein the light-carrying element (18) is an optical waveguide comprising glass or plastic.

3. The optical sensor of claim 1, wherein the light-carrying element (18) is an optical waveguide comprising glass or plastic.

4. The optical sensor of claim 1, wherein the light-carrying element (18) is a plate or other suitably shaped body that can carry the light.

5. The optical sensor of claim 1, wherein the light-carrying element (18) has separate optical waveguides for the delivery and return of the electromagnetic waves.

6. The optical sensor of claim 1, wherein the light-carrying element (18) has a coupling element (20), by means of which a deflection of the electromagnetic waves onto the sensor region (16) is effected.

7. The optical sensor of claim 6, wherein the coupling element (20) is formed of an elbow (26) or prism (28) or by structuring (30) of the surface of the light-carrying element.

8. The optical sensor of claim 1, wherein a sensor-active substance (24) that in the presence of a measurement substance changes its coefficient of refraction or color is applied in the sensor region (16).

9. The optical sensor of claim 1 wherein the coupling element (20) and the light-carrying element (18) form a structural unit.

10. The optical sensor of claim 8, the retroreflector (10) and a substrate (22) of the measurement substance (24) form a structural unit.

11. The use of an optical sensor of claim 1, as a rain sensor in motor vehicles.

12. The use of an optical sensor of claim 8 as a sensor for various substances that are in the form of liquid, aerosol, or in solution or in gaseous form.

13. The optical sensor of claim 1, wherein the retroreflector (10) is disposed inside a windshield (12).

14. The optical sensor of claim 1, wherein the hologram is disposed inside a windshield (12).

15. The optical sensor of claim 14, wherein an adhesive film (40) disposed in the windshield (12) is itself at least partly embodied as a hologram (38).

\* \* \* \* \*